(12) United States Patent
Chen et al.

(10) Patent No.: US 9,355,440 B1
(45) Date of Patent: May 31, 2016

(54) DETECTION OF SELECTED DEFECTS IN RELATIVELY NOISY INSPECTION DATA

(71) Applicant: KLA-Tencor Corporation, Milpitas, CA (US)

(72) Inventors: Haiguang Chen, Mountain View, CA (US); Michael D. Kirk, San Jose, CA (US); Stephen Biellak, Sunnyvale, CA (US); Jaydeep Sinha, Livermore, CA (US)

(73) Assignee: KLA-Tencor Corp., Milpitas, CA (US)

( * ) Notice: Subject to any disclaimer, the term of this patent is extended or adjusted under 35 U.S.C. 154(b) by 738 days.

(21) Appl. No.: 13/649,080

(22) Filed: Oct. 10, 2012

(51) Int. Cl.
*G06T 7/00* (2006.01)
*G01N 21/88* (2006.01)

(52) U.S. Cl.
CPC .......... *G06T 7/0004* (2013.01); *G01N 21/8851* (2013.01); *G01N 2021/8887* (2013.01); *G06T 2207/20061* (2013.01); *G06T 2207/30148* (2013.01)

(58) Field of Classification Search
CPC .................. G06T 5/50; G06T 7/0004; G06T 2207/20061; G06T 2207/30148; G06K 2009/2045; G01N 21/88; G01N 21/8806; G01N 21/8851; G01N 21/8887; G01N 21/9501
See application file for complete search history.

(56) References Cited

U.S. PATENT DOCUMENTS

| | | | |
|---|---|---|---|
| 3,069,654 A | 12/1962 | Hough | |
| 5,418,892 A | 5/1995 | Aghajan et al. | |
| 5,430,810 A | 7/1995 | Saeki | |
| 5,471,066 A | 11/1995 | Hagiwara | |
| 6,229,928 B1 | 5/2001 | Matsuzawa | |
| 6,268,935 B1 | 7/2001 | Kingetsu | |
| 6,292,583 B1 | 9/2001 | Maruo | |
| 6,324,299 B1 | 11/2001 | Sarachik et al. | |
| 6,330,354 B1 | 12/2001 | Companion et al. | |
| 6,399,953 B1 * | 6/2002 | Kitamura | 250/491.1 |
| 6,408,105 B1 | 6/2002 | Maruo | |
| 6,544,805 B2 | 4/2003 | Holcman et al. | |
| 6,574,366 B1 | 6/2003 | Fan | |
| 6,650,135 B1 * | 11/2003 | Mautz et al. | 324/750.16 |
| 6,665,449 B1 | 12/2003 | He et al. | |
| 6,810,139 B2 | 10/2004 | Smilansky et al. | |
| 7,057,721 B2 | 6/2006 | Gardner et al. | |
| 7,373,277 B1 | 5/2008 | Wu et al. | |
| 7,711,521 B1 * | 5/2010 | Wu et al. | 702/185 |
| 8,223,327 B2 | 7/2012 | Chen et al. | |
| 2002/0181756 A1 | 12/2002 | Shibuya et al. | |
| 2003/0132405 A1 | 7/2003 | Some | |
| 2004/0064269 A1 | 4/2004 | Shibuya et al. | |
| 2005/0282299 A1 * | 12/2005 | Kim et al. | 438/14 |
| 2006/0181700 A1 * | 8/2006 | Andrews et al. | 356/237.2 |
| 2011/0144943 A1 * | 6/2011 | Veeraraghavan et al. | 702/167 |

* cited by examiner

*Primary Examiner* — Andrew W Johns
(74) *Attorney, Agent, or Firm* — Ann Marie Mewherter

(57) ABSTRACT

Methods and systems for detection of selected defects in relatively noisy inspection data are provided. One method includes applying a spatial filter algorithm to inspection data acquired across an area on a substrate to determine a first portion of the inspection data that has a higher probability of being a selected type of defect than a second portion of the inspection data. The selected type of defect includes a non-point defect. The inspection data is generated by combining two or more raw inspection data corresponding to substantially the same locations on the substrate. The method also includes generating a two-dimensional map illustrating the first portion of the inspection data. The method further includes searching the two-dimensional map for an event that has spatial characteristics that approximately match spatial characteristics of the selected type of defect and determining if the event corresponds to a defect having the selected type.

35 Claims, 2 Drawing Sheets

DETECTION OF SELECTED DEFECTS IN RELATIVELY NOISY INSPECTION DATA

BACKGROUND OF THE INVENTION

1. Field of the Invention

The present invention generally relates to methods and systems for detection of defects in relatively noisy inspection data.

2. Description of the Related Art

The following description and examples are not admitted to be prior art by virtue of their inclusion in this section.

Inspection of semiconductor wafers is and will continue to be of significant importance in semiconductor manufacturing. In addition, the ability of inspection tools or systems to detect a range of defect types may determine how well semiconductor fabrication processes can be monitored and controlled. Consequently, there have been significant efforts in improving the processing of inspection data to increase the accuracy with which defects can be detected.

Most inspection data processing involves two steps: defect detection and then classification. For instance, on many commercially available inspection systems, defects are found by detecting point defects via signal thresholding on individual data points in simple one-dimensional scans. Individual point defects may then be displayed on a point defect map or organized into another format. The point defect map is then post-processed to recognize if several of the points fall roughly into a two-dimensional shape, at which point that collection of points is labeled or classified as a specific defect instead of as individual particle defects.

There are, however, several disadvantages to the above methods of inspection data processing for detecting the presence of particular types of defects. In particular, these methods can be relatively inaccurate when detecting defects in relatively noisy inspection data. For example, as described above, simple one-dimensional scans only generate raw signals at individual points on the substrate, and every encounter with a two-dimensional surface anomaly is treated as a disconnected collection of point defects. Therefore, signal thresholding yields a defect map determined solely by signal strength at the individual points. Consequently, portions of faint two-dimensional defects may be lost to background noise due to failure of some of its associated point defect signals to exceed the threshold. As a result, the above-described methods for detecting defects may be substantially inaccurate when detecting defects in noisy inspection data since many defects may not be detected at all. In addition, the above-described methods for detecting defects may be substantially inaccurate in detecting the types of defects that are present on a substrate since portions of defects may not be detected thereby increasing the probability of misclassification of defects.

Accordingly, it may be advantageous to develop methods and systems for detecting defects on a substrate that are substantially accurate for detecting a range of defect types, particularly in relatively noisy inspection data.

SUMMARY OF THE INVENTION

The following description of various embodiments is not to be construed in any way as limiting the subject matter of the appended claims.

One embodiment relates to a computer-implemented method for detecting defects on a substrate. The method includes applying a spatial filter algorithm to inspection data acquired across an area on the substrate to determine a first portion of the inspection data that has a higher probability of being a selected type of defect than a second portion of the inspection data. The selected type of defect includes a non-point defect. The inspection data includes inspection data generated by combining two or more raw inspection data corresponding to substantially the same locations on the substrate. The method also includes generating a two-dimensional map illustrating the first portion of the inspection data. In addition, the method includes searching the two-dimensional map for an event that has spatial characteristics that approximately match spatial characteristics of the selected type of defect. The method further includes determining if the event corresponds to a defect having the selected type. The applying, generating, searching, and determining steps are performed using a computer system.

The method described above may be performed as described further herein. In addition, the method described above may include any other step(s) of any other method(s) described herein. Furthermore, the method described above may be performed by any of the systems described herein.

Another embodiment relates to a computer-readable medium storing program instructions executable on a computer system for performing a computer-implemented method for detecting defects on a substrate. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

An additional embodiment relates to a system configured to detect defects on a substrate. The system includes an inspection subsystem that includes two or more detectors. The two or more detectors are configured to detect light from the substrate and to generate raw inspection data in response to the detected light. The system also includes a computer subsystem configured for applying a spatial filter algorithm to inspection data acquired across an area on the substrate to determine a first portion of the inspection data that has a higher probability of being a selected type of defect than a second portion of the inspection data. The selected type of defect includes a non-point defect. The inspection data includes inspection data generated by combining two or more of the raw inspection data generated by the two or more detectors corresponding to substantially the same locations on the substrate. The computer subsystem is further configured for performing the steps of the method described above. The system may be further configured as described herein.

Another embodiment relates to a computer-implemented method for detecting defects on a substrate. The method includes converting information generated by inspection of a substrate into polar space. The method also includes identifying periodic components in the converted information. The periodic components are not periodic component due to dies formed on the substrate or structures formed in the dies. In addition, the method includes determining if the periodic components correspond to defects on the substrate. The converting, identifying, and determining steps are performed using a computer system.

The method described above may be performed as described further herein. In addition, the method described above may include any other step(s) of any other method(s)

described herein. Furthermore, the method described above may be performed by any of the systems described herein.

BRIEF DESCRIPTION OF THE DRAWINGS

Further advantages of the present invention will become apparent to those skilled in the art with the benefit of the following detailed description of the preferred embodiments and upon reference to the accompanying drawings in which.

Figure 1:
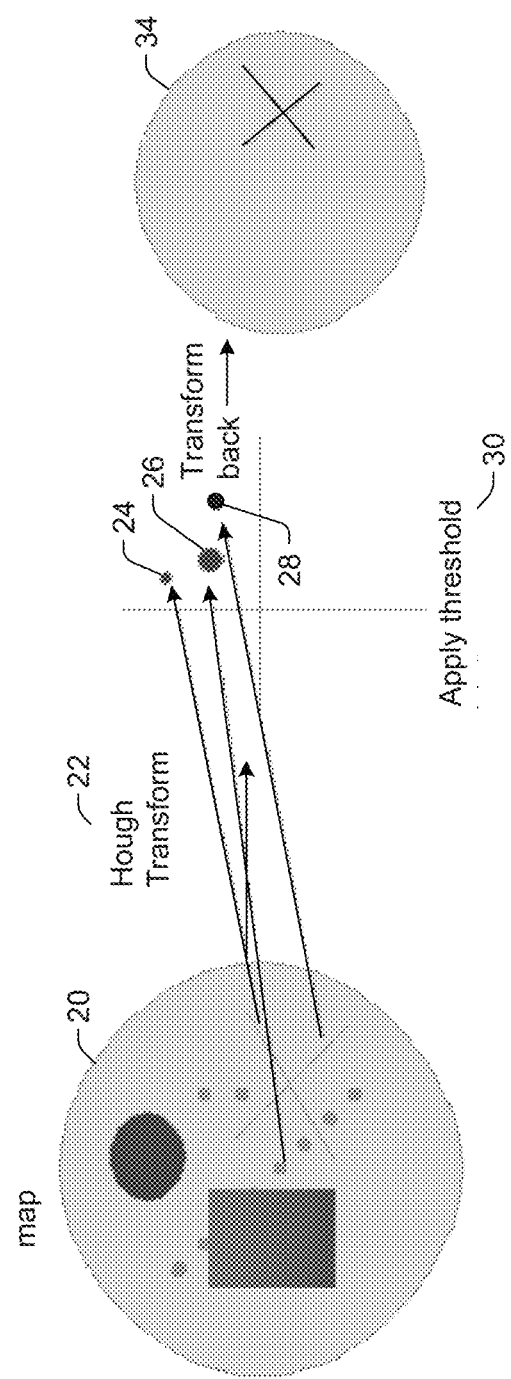
FIG. 1 is a conceptual diagram illustrating one example of defect detection results that can be generated using the computer-implemented methods described herein.

While the invention is susceptible to various modifications and alternative forms, specific embodiments thereof are shown by way of example in the drawings and are herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

In general, the embodiments described herein relate to detecting two-dimensional defects on a substrate in relatively noisy inspection data. For example, one embodiment relates to a computer-implemented method for detecting defects on a substrate.

As used herein, the term "raw inspection data" generally refers to data acquired by inspection of a substrate that has not been processed to alter the signal-to-noise ratio of the data. For example, raw inspection data may be data that has been translated from one form to another (e.g., digitized or transformed from one space to another). In addition, raw inspection data may be data that has been segmented into portions of raw inspection data, all of which has been acquired in one inspection of a substrate. However, the signal-to-noise ratio of the raw inspection data will be approximately equal to the signal-to-noise ratio of the light detected by the inspection subsystem that is used to generate output corresponding to the raw inspection data.

The raw inspection data may also be acquired by inspecting the front side of a substrate or the back side of a substrate. In the case of a wafer, the "front side" is defined as the surface of the wafer upon which devices will or can ultimately be formed. The "back side" is defined as the surface of the wafer upon which devices will not or cannot be fabricated.

The raw inspection data may contain a significant amount of noise. For example, the raw inspection data may have a relatively low signal-to-noise ratio. Usually, such raw inspection data cannot be used for defect detection since currently available methods for defect detection generally detect defects based solely on the signal strength at individual data points. For example, portions of relatively faint two-dimensional defects may be lost to background noise due to failure of its associated point defect signals to exceed a threshold.

However, since the methods and systems described herein use the spatial characteristics of a selected type of defect to recognize defects among the total field of competing signals, these methods and systems can extract very faint portions of a two-dimensional defect from a background of roughly 1.0 signal-to-noise ratio. Therefore, these methods can detect defects in relatively noisy inspection data with significant accuracy in addition to many other advantages over the currently used methods.

Furthermore, the methods and systems described herein may be used to improve and extend the inspection capability of inspection hardware and configurations. For example, hardware architectures in wafer inspection tools, which generally include laser, optical path, and collector configurations, largely influence the relative signal of defects compared to overall field signal. Of course, distinctions in these architectures can afford considerable advantages for capturing a range of defect types over a range of sensitivities. However, as each architecture is pushed up against the technical limits of its designed performance, there becomes even greater value in enabling a given tool to better leverage its raw signal to generate more meaningful results. For example, raw inspection data, which is produced by an optical system that is optimized for particle defect detection but not scratches, may be processed as described herein to increase the accuracy with which scratches may be detected in the raw inspection data.

In some embodiments, the raw inspection data may include data that is acquired by optical inspection of the substrate. Optical inspection of a substrate may include scanning and imaging the substrate. Therefore, in one embodiment, the raw inspection data may include raw scan images of the substrate. Optical inspection data may be particularly useful in the methods and systems described herein since the optical inspection data can be acquired across a relatively large area of a substrate (e.g., an entire area of a substrate surface) in a relatively short amount of time. In addition, since the raw inspection data can contain a significant amount of noise without reducing the accuracy of the defect detection methods and systems described herein, the optical inspection data may be acquired using a number of different optical inspection systems, which may or may not be optimized for detection of the selected type of defect. The optical inspection systems that can be used with the methods and systems described herein include different types of optical systems such as reflectometers, scatterometers, ellipsometers, darkfield and/or brightfield optical subsystems, or some combination thereof. The optical inspection systems may also be non-imaging and/or imaging systems. In addition, the optical inspection systems may be single wavelength systems, spectroscopic systems, or some combination thereof.

However, it is to be understood that the methods and systems described herein may be used with any system that can generate inspection data across a two-dimensional space on a substrate. Examples of such systems include, but are not limited to, e-beam systems (e.g., scanning electron microscopes, etc.), scanning probe microscopes (e.g., atomic force microscopes, scanning tunneling microscopes, etc.), and x-ray systems (e.g., x-ray reflectometers, x-ray diffractometers, etc.).

As used herein, the term "non-point defect" generally refers to any defect that has some lateral extent in two-dimensions across a substrate, particularly across more than one measurement point on the substrate. In contrast, a "point defect" is generally defined as a defect that is detected at generally one measurement point on a substrate, and is therefore not considered to have any measurable lateral extent in two-dimensions across the substrate. It is to be noted that point defects can and are picked up in one or two adjacent data points, not because they are bigger than a data point but because scanning spots can be overlapped to help determine point defect location. This overlap is done not for understanding the spatial extent of the defect, but rather to help "triangulate" the defect positions (remember that these point defects are orders of magnitude smaller than our spot size). An extended defect is one that shows up in multiple scans (e.g., more than two) and each element of the extended defect can have a measured different xy location.

The term "selected type of defect" refers to a non-point defect. In one embodiment, the selected type of defect may be a scratch. The scratch may have an approximately linear shape. However, the scratch may have any other shape as well (e.g., nonlinear, circular, ellipsoidal, arcuate, etc.). Although the methods and systems described herein have proven to be particularly effective for detecting scratches, the methods and systems described herein may also be used to detect other types of non-point defects. For example, the selected type of defect may be a blob, a fiber, a chuck or handler pattern, slip lines, boat marks, straight line structures, or any other defect that has some lateral extent in two-dimensions. As used herein, the term "selected type of defect" also refers to any type of defect that is of interest to a user. In particular, the computer-implemented methods and systems described herein allow users who are interested in finding specific, prescribed two-dimensional defects to extract those defects from raw inspection data such as wafer imaging data despite relatively weak signal-to-noise signatures.

The type of defect that is selected for detection may also vary depending on the substrate and processes that have been performed on the substrate. For example, if the substrate is a wafer that has been polished (e.g., by chemical-mechanical polishing), then the selected type of defect may be a scratch. The particular shape of the scratch may also vary depending on the particular process that was used to polish the wafer. In another example, if the substrate is a wafer that has been cleaned (e.g., in a wet or dry cleaning process), then the selected type of defect may be a blob. In one embodiment, the selected type of defect includes defects having limited orientations and location regions defined by a material structure on the substrate and one or more processes performed on the substrate. In addition, the selected type of defect may include defects having only specific orientations.

As used herein, the term "event" generally refers to a portion of a two-dimensional map that has a greater probability of corresponding to a selected type of defect than another portion of the two-dimensional map.

As used herein, the term "spatial characteristics" is generally defined as characteristics that define the two-dimensional extent of a non-point defect across a substrate. Therefore, the spatial characteristics define the two-dimensional shape of the non-point defect as well as the expected lateral dimensions of the non-point defect in the two dimensions. The spatial characteristics may be expressed using any form known in the art such as an equation, a function, an algorithm, a model, or some combination thereof. In addition, since, as described above, the selected type of defect may vary depending on the processing performed on the substrate, the spatial characteristics of the selected type of defect may be determined based on processing of the substrate.

The computer-implemented method includes applying a spatial filter algorithm to inspection data acquired across an area on the substrate to determine a first portion of the inspection data that has a higher probability of being a selected type of defect than a second portion of the inspection data. It is to be noted that the terms "first" and "second" are used herein only to distinguish between different portions of data and are not to be construed in any other manner.

In some embodiments, the inspection data may include data that is acquired across an area of the substrate that equals approximately an entire area of a surface of the substrate. In other words, the inspection data may include inspection data acquired by a scan or an inspection of substantially an entire surface of the substrate. Therefore, unlike currently used defect detection methods that analyze inspection data on a point-by-point basis, the methods described herein detects defects by processing inspection data that spans a relatively large area on the surface of a substrate. In addition, unlike currently used defect detection methods, the methods described herein take advantage of the shape of two-dimensional defects, when prescribed a priori, to recognize these defects among the total field of competing signals as described further herein.

Alternatively, the inspection data may include data that is acquired across a portion of a surface of the substrate. For example, an entire surface of a substrate may be scanned during inspection, and the inspection data may be segmented into portions, each or some of which may be used in the computer-implemented methods described herein. Segmenting the data in such a manner may reduce the time in which processing of the data is completed, particularly if multiple segments are processed in parallel (e.g., using a parallel processor). In one example, the inspection data may be segmented into quadrants on the substrate. However, the inspection data may be segmented into any number of portions. The portions of the inspection data are preferably large enough so that the likelihood that an entire defect resides within one portion of the inspection data is relatively large. Therefore, the size of the portions that the inspection data is segmented into may vary depending on, for example, the lateral dimensions of the selected type of defect. In addition, the size of the portions of the inspection data will be substantially larger than an individual point in a scan of the substrate. Consequently, even if the inspection data is segmented, the methods and systems described herein will be unlike the currently used defect detection methods as described above.

The inspection data to which the spatial filter algorithm is applied includes inspection data generated by combining two or more raw inspection data corresponding to substantially the same locations on the wafer. In one embodiment, the two or more raw inspection data are generated by different detectors of the same inspection system, which may be configured as described further herein. In one such embodiment, the different detectors are coupled to different collectors of the same inspection system, which may be configured as described further herein. In another such embodiment, the different detectors are configured to detect light scattered from the substrate at different scattering angles, and the different detectors are not different detection elements of the same detector, which may be configured as described further herein. For example, the different detectors are not different pixels of one detector. In some embodiments, as described further herein, the two or more raw inspection data are generated simultaneously. In other embodiments, as described further herein, the two or more raw inspection data are generated sequentially.

In one embodiment, combining the two or more raw inspection data includes applying a mathematic function to the two or more raw inspection data corresponding to the substantially the same locations on the wafer. For example, the raw inspection data may include raw scan maps, which may be combined with some mathematic function before or during the spatial filter algorithm application step. The mathematic function may include, for example, a simple addition or averaging function. However, the mathematic function may include more complicated functions and any suitable function known in the art. Therefore, the inspection data to which the spatial filter algorithm is applied is different than the raw inspection data. For example, the inspection data may have a different signal-to-noise ratio than the raw inspection data. Preferably, the mathematic function that is used for the combining step results in inspection data that has greater signal-to-noise ratio than the raw inspection data that is combined. In particular, different detectors of the same inspection system may generate different signal-to-noise ratios at the same location on a wafer due to different levels of defect scattering and noise detected by the different detectors. Therefore, by combining the two or more raw inspection data, noise that is not spatially coincident can be reduced or even eliminated in the inspection data generated by the combining step. Combining the two or more raw inspection data may be further performed as described in U.S. Pat. No. 8,223,327 to Chen et al., which is incorporated by reference as if fully set forth herein.

In one embodiment, applying the spatial filter algorithm may include extracting the first portion of the inspection data. In these embodiments, the spatial filter algorithm may also be used to determine two or more portions of the inspection data that have a higher probability of being a selected type of defect than other portions of the inspection data. In addition, the spatial filter algorithm may extract two or more portions of the inspection data that are more likely to be a selected type of defect than other portions of the raw inspection data. In one example, a two-dimensional line filter may be applied to the inspection data to extract portions of the inspection data that may be the selected type of defect. The portions of the extracted inspection data may be very faint (i.e., have relatively low intensity), and yet may be extracted by the spatial filter algorithm.

In another embodiment, the computer-implemented method may include accentuating the first portion of the inspection data. Accentuating the first portion of the data may include altering a characteristic of the data points that make up the first portion of the inspection data. For example, the intensity or color of the data points that make up the first portion of the inspection data may be altered. In addition, if two or more portions of the inspection data are identified by the spatial filter algorithm, each of the two or more portions of the inspection data may be accentuated as described above. Each of the two or more portions of the inspection data may be accentuated to the same or different degrees and/or in the same or different ways. In addition, the degree to, and the manner in, which a portion of the inspection data is accentuated may vary depending on characteristics of the portion of the inspection data as well as characteristics of other portions of the inspection data.

In this manner, the first portion of the inspection data may be more easily distinguished from other portions of the inspection data in subsequent data processing. As such, the spatial filter algorithm can be used to better enhance the spatial features of the inspection data and to improve the signal-to-noise ratio. For example, in scratch detection, the line structures in the image data may be enhanced. This preprocessing stage provides a superior detection performance.

In the embodiments described above, the spatial filter algorithm can also specify the orientations of the defects that it will report. For example, the spatial filter algorithm may be set up to search for only scratch defects oriented in the vertical and horizontal directions. This feature can be very useful for slip line detection in wafer inspection.

The computer-implemented method also includes generating a two-dimensional map of the substrate. The two-dimensional map preferably illustrates the first portion of the inspection data identified above. For example, the two-dimensional map may be generated using the extracted data. Therefore, the two-dimensional map may illustrate only the portion(s) of the data that have a higher probability of being a selected type of defect. Alternatively, the two-dimensional map may illustrate all of the inspection data including the portion(s) of the inspection data that were accentuated. In this manner, the two-dimensional map may have a relatively good signal-to-noise ratio. In another alternative, the two-dimensional map may illustrate only the accentuated portion(s) of the inspection data.

The method includes searching the two-dimensional map for an event that has spatial characteristics that approximately match spatial characteristics of a selected type of defect. An event does not have to have spatial characteristics that exactly match the spatial characteristics of the selected type of defect. However, an event should have spatial characteristics that match the spatial characteristics of the selected type of defect within some margin of error. In this manner, searching the raw two-dimensional map identifies one or more events that have some likelihood of corresponding to the selected type of defect.

Searching the two-dimensional map for an event may include, in one embodiment, applying a geometrical recognition algorithm to the two-dimensional map. Many geometrical recognition algorithms are known in the art, and selection of an appropriate geometrical recognition algorithm may vary depending on the spatial characteristics of the selected type of defect. For example, in one embodiment, the spatial characteristics of the selected type of defect may be substantially linear. In such an embodiment, a Hough transform may be applied to the two-dimensional map to search for events that have spatial characteristics that approximately match the spatial characteristics of the selected type of defect. For example, the Hough transform may be applied to the two-dimensional map to convert the data into a new space representation. This representation shows objects having a particular shape in point-like events that can then be thresholded as described below.

Further description of the Hough transform can be found in U.S. Pat. No. 3,069,654 to Hough, which is incorporated by reference as if fully set forth herein. In addition, the Hough transform that is used in this method may be a modified version of the Hough transform or a generalized Hough transform (GHT). For example, the Hough transform may be modified such that events having nonlinear spatial characteristics can be searched for in the two-dimensional map. Other examples of geometrical recognition algorithms that may be used in this method include the Sobel operator, the Prewitt operator, the Kirsch operator, and Robert's operator. In addition, in some embodiments, searching the two-dimensional map may include applying a line enhancement filter to the two-dimensional map. Other appropriate algorithms may include a Fourier transform for periodic defects and a circle transform for circular shaped defects. In addition, a specialized transform or algorithm may be developed for a particular type of defect. For example, portions of one or more defect maps that are known to correspond to a particular type of defect may be used as templates to generate a transform or algorithm that can then be used to recognize geometrical two-dimensional shapes in two-dimensional maps. Furthermore, multiple transforms may be applied to the two-dimensional map separately or in combination.

As described above, the selected type of defect may include slip lines and boat marks, where the defects are more like straight-line structures and have limited orientations and location regions defined by the wafer material structure and the wafer processing involved. For example, slip lines may be located in the wafer edge region and may be orthogonal to the wafer edge. Boat marks (e.g., EPI-pin marks) may be located at a certain wafer radius and separated by fixed rotation angles. In these cases, the filters can be designed to carry out a more focused search and enhancement only in the neighborhood of these major orientations. As a result, more sensitive and robust detection can be performed with less processing time.

The computer-implemented method also includes determining if the event corresponds to a defect having the selected type. In other words, this step involves taking events that have been identified as potentially corresponding to defects having the selected type and comparing them to some criteria to determine whether or not they actually correspond to the selected type of defect. In one embodiment, determining if the event corresponds to a selected type of defect includes applying a thresholding algorithm to the event. For example, a thresholding algorithm may be applied to the events identified by the application of the Hough transform to determine if the events correspond to line defects. In addition, multiple thresholding algorithms may be applied to the event simultaneously or sequentially.

The thresholding algorithm can be derived in the transformed space and may be combined with one-dimensional defect information. For example, the thresholding algorithm may compare one or more characteristics of the events to a predetermined threshold for each of the characteristic(s) in the transformed space. If the characteristic(s) of an event exceed the predetermined threshold(s), then the event may be determined to be a defect of the selected type. The characteristic(s) that are compared by the thresholding algorithm(s) may vary depending on the transformed space, the characteristic(s) of the selected type of defect and, in some instances, characteristics of the two-dimensional map. Thresholding algorithms are generally known in the art and, thus, will not be described further herein. In addition, thresholding algorithms may be modified depending on the characteristic(s) that are to be compared, and such modifications will be obvious to one of ordinary skill in the art. However, any appropriate algorithm or model known in the art may be used to determine if the event corresponds to a selected type of defect.

After thresholding the events and extracting those which are determined to correspond to the selected type of defect, the location of those events may be used to create a two-dimensional mask. The two-dimensional mask preferably has the same size as the two-dimensional map and is used to remove the non-selected types of defects from the two-dimensional map and to keep the selected type of defects. Therefore, the two-dimensional mask and the two-dimensional map may be used to generate a processed two-dimensional map of the substrate illustrating only the defects that are determined to be the selected type of defects. Since the processed two-dimensional map illustrates only the defects that have been determined to be the selected type of defect, the method can be used to produce maps that clearly illustrate only those defects which are of interest to the user. In addition, more than one two-dimensional map may be generated for one substrate. Each of the two-dimensional maps may illustrate different selected types of defects.

The processed two-dimensional map may be further processed, for example, by combining the processed two-dimensional map with other defect maps or other two-dimensional maps of the substrate, and/or generating other transformed maps of the substrate. The processing may also or alternatively include applying another thresholding algorithm to the raw inspection data and/or any other processing known in the art.

Although the embodiments of the computer-implemented method have been described with respect to one event, it is to be understood that searching the two-dimensional map may identify two or more events, each of which have spatial characteristics that approximately match the spatial characteristics of a selected type of defect. Therefore, the method may be used to detect multiple events on the substrate substantially simultaneously, each of which may correspond to the selected type of defect. The method may also include determining if each of (or at least some of) the two or more events correspond to the selected type of defect. Such determinations may be performed as described above. Determining whether or not each of (or at least some of) the multiple events correspond to the selected type of defect may be performed sequentially or substantially simultaneously.

Furthermore, although the embodiments of the computer-implemented method have been described with respect to one selected type of defect, it is to be understood that the method may be used to detect more than one selected type of defect sequentially or substantially simultaneously. For example, in one embodiment, the above-described computer-implemented method may be performed repeatedly, each time for a different type of defect. Alternatively, more than one selected type of defect may be detected substantially simultaneously. For example, the computer-implemented method may include, in some embodiments, substantially simultaneously searching the two-dimensional map for one or more events that have spatial characteristics that approximately match the spatial characteristics of more than one selected type of defect. In some embodiments, parallel processing may be used to search the two-dimensional map for events that match more than one selected type of defect at the same time.

Such an embodiment of the method may also include determining if the one or more events correspond to defects having one of the more than one selected type. In particular, this step involves determining only whether or not the event(s) correspond to the selected type of defect that their spatial characteristics approximately match. Determining whether or not each of (or at least some of) the multiple events correspond to a selected type of defect may be performed sequentially or substantially simultaneously. Determining whether or not each of the multiple events correspond to a selected type of defect may include applying a thresholding algorithm, another algorithm, or model to the events, as described further above. In addition, determining if the events correspond to each type of two-dimensional defect may be performed independently with different thresholding algorithms.

The computer-implemented method may, in some embodiments, include acquiring the raw inspection data. Acquiring the raw inspection data may include performing optical inspection of a substrate. The optical inspection may be performed using any of the optical systems described herein or any other optical inspection system known in the art. Examples of optical inspection systems that may be used to acquire the raw inspection data include the Surfscan SPx based inspection systems and other optical inspection systems that are commercially from KLA-Tencor, Milpitas, Calif. Alternatively, acquiring the raw inspection data may include performing non-optical inspection of a substrate. For example, the raw inspection data may be acquired using one or more of the e-beam, scanning probe, or x-ray systems described herein and/or any other non-optical inspection system known in the art.

Acquiring the raw inspection data may include scanning an area on the substrate. In addition, acquiring the raw inspection data may include imaging an area on the substrate. Therefore, the raw inspection data may include raw scan images. For example, acquiring the raw inspection data may include detecting light reflected from an area on the substrate with a detector that has a two-dimensional photosensitive array (e.g., a charge-coupled device (CCD) camera or a time delay integration (TDI) camera) to form an image of the area. Such detectors are known in the art, and an appropriate detector may be selected based on the overall configuration of the optical inspection system.

Alternatively, acquiring the raw inspection data may include detecting light reflected from the substrate using a point detector such as a photomultipler tube (PMT). Such detectors are known in the art. Therefore, the raw inspection data may include inspection data at individual points on the substrate, which are arranged into a two-dimensional format based on positional information about the individual points. The positional information about the individual points may be recorded during inspection as is known in the art. As a result, the raw inspection data may include a number of inspection data points that are acquired across an area on the substrate to which collectively a spatial filter algorithm may be applied as described above. Consequently, unlike the currently available methods in which individual data points are examined individually for the presence of a defect at each point, in the methods described herein, individual data points may be used as the raw inspection data, but a collection of individual data points are used in combination to detect the presence of a selected type of defect.

The computer-implemented methods described above may include any other step(s) described herein. For example, in one embodiment, the method includes converting information generated by inspection of the substrate into polar space, identifying periodic components in the converted information, the periodic components are not periodic components due to dies formed on the substrate or structures formed in the dies, and determining if the periodic components correspond to defects on the substrate, all of which may be performed as described further herein.

Each of the steps of the computer-implemented method (e.g., applying the spatial filter algorithm, generating a two-dimensional map, searching the two-dimensional map, and determining if the event corresponds to a defect having the selected type) may be performed using a computer system, which may be further configured as described herein.

FIG. 1 is a conceptual diagram illustrating one example of defect detection results that can be generated using the computer-implemented method described above. In this example, the substrate is a wafer, and the surface that is inspected is the front side of the wafer. As shown in FIG. 1, two-dimensional map 20 can be generated as described above. For example, the two-dimensional map may be created from data extracted by the spatial filter algorithm or accentuated data (possibly in combination with non-accentuated data).

As shown in FIG. 1, Hough transform 22 is applied to the two-dimensional map to search for events that have spatial characteristics that approximately match spatial characteristics of a selected type of defect. In this example, the selected type of defect is a scratch having a substantially linear shape. The Hough transform converts the two-dimensional map into a new space representation. This representation shows linear shaped objects on the two-dimensional map in point-like events 24, 26, and 28. As shown in FIG. 1, events 24 and 28 correspond to scratches, but event 26 corresponds to a number of individual point defects that happen to fall in a line.

The method determines which of the events correspond to the selected type of defect by applying threshold 30 to events 24, 26, and 28. The threshold can be derived in the new space or combined with one-dimensional defect characteristics. For example, threshold 30 may compare one or more characteristics of the two-dimensional map corresponding to individual events to one or more characteristics of the selected type of defect. In this example, the threshold may compare the distance between individual point defects on the two-dimensional map that make up events 24, 26, and 28. If the individual point defects of an event are sufficiently close together, then the threshold may determine that the event corresponds to a scratch. In this manner, events 24 and 28 will be determined as events that correspond to a scratch, but since the individual point defects of event 26 are relatively far apart, as shown in the two-dimensional map, event 26 will be determined as an event that does not correspond to a scratch.

After thresholding the events and extracting those which are determined to correspond to the selected type of defect, the location of those events may be used to create a two-dimensional mask, which can be used to remove non-selected types of defects from the two-dimensional map thereby creating a processed two-dimensional map. As shown in FIG. 1, processed two-dimensional map 34 illustrates only the defects that are scratches. As such, processed two-dimensional map 34 provides a much simpler and clearer representation of the defects of interest than two-dimensional map 20.

Figure 2:
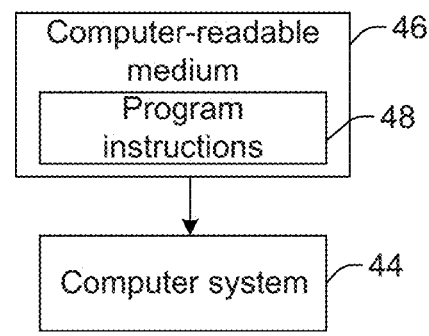
FIG. 2 is a block diagram illustrating one embodiment of a non-transitory computer-readable medium storing program instructions executable on a computer system for performing one or more computer-implemented methods described herein.

An additional embodiment relates to a non-transitory computer-readable medium storing program instructions executable on a computer system for performing a computer-implemented method for detecting defects on a substrate. One such embodiment is shown in FIG. 2. In particular, as shown in FIG. 2, non-transitory computer-readable medium 46 includes program instructions 48 executable on computer system 44. The computer-implemented method includes the steps of the method described above. The computer-implemented method for which the program instructions are executable may include any other step(s) described herein.

Program instructions 48 implementing methods such as those described herein may be stored on computer-readable medium 46. The computer-readable medium may be a storage medium such as a read-only memory, a random access memory, a magnetic or optical disk, or a magnetic tape or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), or other technologies or methodologies, as desired.

The computer system may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer system may also include any suitable processor known in the art such as a parallel processor. In addition, the computer system may include a computer platform with high speed processing and software, either as a standalone or a networked tool.

Figure 3:
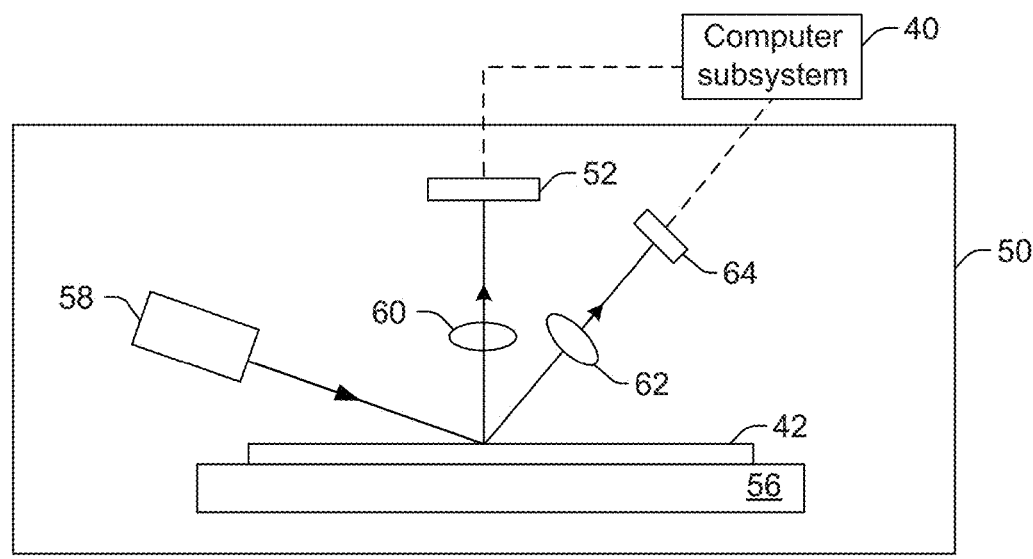
FIG. 3 is a schematic diagram illustrating one embodiment of a system configured to detect defects on a substrate.

FIG. 3 illustrates one embodiment of a system configured to detect defects on substrate 42. The system includes inspection subsystem 50. Inspection subsystem 50 is shown in FIG. 3 as an optical inspection subsystem that is configured to detect light scattered from a substrate. The inspection subsystem includes stage 56 upon which substrate 42 may be disposed during inspection. The stage may include any suitable mechanical or robotic assembly known in the art.

The inspection subsystem includes two or more detectors that are configured to detect light from the substrate and to generate raw inspection data in response to the detected light. For example, as shown in FIG. 3, the inspection subsystem may include light source 58, which may include any suitable light source known in the art such as a laser. The light source may be coupled to one or more optical components (not shown in FIG. 1) such as a wavelength filter, a polarizer, one or more lenses, and the like. Together, the light source and the one or more optical components make up the illumination subsystem. As shown in FIG. 3, the light source may be configured to direct light to the substrate at an oblique angle of incidence, which may be any suitable oblique angle of incidence. However, the light source, possibly in combination with the one or more optical components, may be configured to direct the light to the substrate at a normal or near normal angle of incidence and/or at more than one discrete angle of incidence.

Light scattered from the substrate may be collected by optical element 60 and directed to detector 52. Optical element 60 may include any suitable optical element(s) known in the art such as one or more refractive optical elements and/or one or more reflective optical elements. Light scattered from the substrate at different scattering angles than the light collected by optical element 60 may be collected by optical element 62 and directed to detector 64. Optical element 62 may be configured as described with respect to optical element 60. Detectors 52 and 64 may include any suitable detectors known in the art such as CCDs or PMTs. Therefore, as shown in FIG. 3, the different detectors are coupled to different collectors (e.g., optical elements 60 and 62). In addition, as shown in FIG. 3, the different detectors are configured to detect light scattered from the substrate at different scattering angles. In addition, each of the detectors are separate detectors and are not different detection elements of the same detector. For example, the different detectors are not different pixels of the same CCD.

The different detectors may be configured to generate the two or more raw inspection data simultaneously. For example, while the light source or illumination subsystem is directing light to the substrate, both of the different detectors can detect light scattered from the substrate. However, the different detectors may also be configured to generate the two or more raw inspection data sequentially. For example, the inspection subsystem may include one or more shutters positioned between the substrate and one or more of the detectors. The one or more shutters may be positioned in the optical path of one of the detectors while the other detector is detecting light scattered from the wafer and vice versa.

Inspection module 50 may be coupled to computer subsystem 40. For example, one or more components of inspection module 50 may be coupled to computer subsystem 40 by a transmission medium (not shown), which may include "wired" and "wireless" portions. In one such example, detector 52 may be configured to generate raw inspection data that is transmitted across a transmission medium from detector 52 to computer subsystem 40. In a similar manner, detector 64 may be configured to generate raw inspection data that is transmitted across a transmission medium to computer subsystem 40.

Although the inspection subsystem is shown in FIG. 3 to inspect the substrate by detecting light scattered from the substrate, it is to be understood that the inspection subsystem may have any other optical configuration known in the art. For example, the inspection subsystem may be configured to inspect the substrate by detecting light reflected from the substrate. In addition, the inspection subsystem may be configured as an ellipsometer, a reflectometer, a scatterometer, an interferometer, or some combination thereof. The inspection subsystem may also be a non-imaging system, an imaging system, or some combination thereof. In addition, the inspection subsystem may be a single wavelength system (e.g., a single wavelength ellipsometer), a spectroscopic system (e.g., a spectroscopic ellipsometer), or a combination thereof.

Furthermore, although the inspection subsystem is shown in FIG. 3 as an optical inspection system, it is to be understood that the inspection subsystem may be configured as a non-optical inspection subsystem. For example, the inspection subsystem may be configured as an e-beam system (e.g., a scanning electron microscope, etc.), a scanning probe microscope (e.g., an atomic force microscope, a scanning tunneling microscope, etc.), an x-ray system (e.g., an x-ray reflectometer, an x-ray diffractometer, etc.), any other non-optical inspection subsystem known in the art, or some combination thereof. In addition, the inspection subsystem may include a combination of one or more optical inspection subsystems and one or more non-optical inspection subsystems. For example, the inspection subsystem may include an optical inspection subsystem as well as an atomic force microscope.

Computer subsystem 40 may be configured as described above with respect to computer system 44. The computer subsystem is configured for applying a spatial filter algorithm to inspection data acquired across an area on the substrate to determine a first portion of the inspection data that has a higher probability of being a selected type of defect than a second portion of the inspection data, which may be performed as described further herein. The selected type of defect includes a non-point defect, which may include any of such defects described herein. The inspection data includes inspection data generated by combining two or more of the raw inspection data generated by the two or more detectors corresponding to substantially the same locations on the substrate.

The computer subsystem is also configured for generating a two-dimensional map illustrating the first portion of the inspection data, which may be configured as described herein. The computer subsystem is further configured for searching the two-dimensional map for an event that has spatial characteristics that approximately match spatial characteristics of the selected type of defect, which may be performed as described further herein. In addition, the computer subsystem is configured for determining if the event corresponds to a defect having the selected type, which may be performed as described further herein. The system may be further configured according to any other embodiments described herein.

It is noted that FIG. 3 is provided herein to generally illustrate one configuration of an inspection subsystem that may be included in the system embodiments described herein. Obviously, the inspection subsystem configuration described herein may be altered to optimize the performance of the inspection subsystem as is normally performed when designing a commercial inspection system. In addition, the systems described herein may be implemented using an existing inspection system (e.g., by adding functionality described herein to an existing inspection subsystem) such as those that are commercially available from KLA-Tencor. For some such systems, the methods described herein may be provided as optional functionality of the system (e.g., in addition to other functionality of the system). Alternatively, the system described herein may be designed "from scratch" to provide a completely new system.

Additional embodiments described herein relate to using information for defect spatial position distribution of certain defects on a substrate for improved detection sensitivity and purity. For example, another embodiment relates to a different computer-implemented method for detecting defects on a substrate. The defects may include bump defects formed in concentric rings on the substrate, epitaxial (EPI) crown defects, or silicon on insulator (SOI) bump array defects. The EPI crown defects may be located on or near the edge of the substrate. In addition, the SOI defects may include bump dot array defects, slip lines, and possibly other wafer structures and defects. In such instances, the embodiments described herein can be used for detecting bumps located in concentric rings using a complex wafer image with many other surface structures such as slip lines and continuous rings.

The defects may also be located in multiple rings on the substrate, and more than one of the defects may be located at the same radius through the multiple rings. In this manner, the defects may be located on multiple rings of the same radius. Furthermore, the defects may be located in multiple rings on the substrate, and the defects within one of the multiple rings may have substantially the same angular separations between the defects. In this manner, the defects on the same ring may have roughly the same angular separation. The defects may also be located in multiple rings on the substrate, and the defects within one of the multiple rings may have substantially the same properties. For example, the defects on the same ring may have similar defect spatial properties such as defect shape, defect area, and defect polarity.

The defects described above will generally be formed on a front side of wafers (i.e., the surface of wafers on which devices are or will be formed). However, the embodiments described herein can also be used to detect defects on the back sides of wafers (i.e., the surface of wafers on which devices will not or cannot be formed). For example, many defects on the back side of wafers, generated in the wafer manufacturing processes, are strongly related with the patterns on wafer supports used in those processes. In particular, wafer supports such as chucks and stages may have topographical features formed thereon such as ridges, indentations, or openings that may or may not be used to stabilize the wafers being held thereon. For example, some wafer supports such as electrostatic chucks include periodic square-shaped openings formed in a pattern on the wafer supports. The periodic openings may have other shapes such as circular openings through which vacuum may be applied to the back side of wafers to keep them in place. Other wafer supports may have ridges or indentations forming concentric circles on the wafer supports. Such topographical features in the wafer supports may cause defects on the back sides of the wafers, and such defects may have spatial characteristics correlating to those topographical features. The embodiments described herein can therefore be advantageously used to detect such defects on the back sides of wafers. Any inspection system that can be used to produce information by inspection of the back sides of wafers may be used in the embodiments described herein. Such inspection systems may or may not also be used to produce information by inspection of the front sides of wafers. For example, the embodiments described herein may be used to detect defects on both the front side and the back side of a single wafer.

As described further herein, these defect spatial characteristics can be utilized to design effective filtering on the raw data or filtering on initial defect maps for improved detection sensitivity and purity. In addition, as described further herein, the filtering operations can be implemented in the spatial domain directly or the Fourier transform domain.

The method includes converting information generated by inspection of a substrate into polar space. The information may include a wafer surface image, raw inspection data, a defect map, or inspection data generated by combining two or more raw inspection data corresponding to substantially the same locations on the substrate. All such information may be generated as described further herein or in any suitable manner known in the art. The defect map may be an initial defect map of potential defects such as EPI crowns in Cartesian space. The initial defect map may include, for example, white dots showing the locations of potential defects on a black background. In the case of EPI crowns, the initial defect map may show potential EPI crown defects located in one or more rings near the wafer edge as well as other potential defects detected on the wafer.

In this manner, a wafer surface image may be converted into polar space. For example, a wafer surface image in gray scale and Cartesian coordinates can be converted into a gray scale image plotted as a function of polar coordinates (e.g., with the angle in degrees on the x axis and the radius in mm on the y axis). In a similar manner, an initial defect map that has been converted into polar space may include potential defect positions plotted in polar space (e.g., the radius in mm as a function of angle in degrees). Converting the information into polar space may be performed using any suitable function or algorithm known in the art.

The method also includes identifying periodic components in the converted information. The periodic components are not periodic components due to dies formed on the substrate or structures formed in the dies. For example, many defect detection methods for patterned wafers, on which multiple dies are formed each of which include repeating patterned features, include detecting periodic defects on the wafer by determining if multiple defects have been detected at substantially the same location in multiple die or for one patterned feature (e.g., by comparing defect detection results at substantially the same within die positions or at the positions of the same patterned features). Detecting such repeating defects is important because they can indicate a problem with the design for the dies and/or a problem in an interaction between the process used to form the dies and the design. However, the embodiments described herein are designed to detect other types of repeating defects on substrates that may be patterned or unpatterned wafers. For example, certain processes like EPI processes and SOI processes may form defects in a characteristic pattern on wafers that is independent of the patterns formed on the wafer due to the dies on the wafer. However, the properties of those characteristic patterns may be utilized as described herein to advantageously detect certain types of defects such as those described above on substrates even in the presence of significant noise.

In one embodiment, identifying the periodic components includes determining a one-dimensional autocorrelation function (ACF) for different radiuses in the converted information and identifying the periodic components based on peaks in the ACF. For example, identifying the periodic components may include calculating the one-dimensional ACF for each radius image data vector and identifying the existence of the periodic components by ACF peaks. In one such example, using the polar space information, a gray scale image of ACF: Radius (mm) as a function of correlation lag (degrees) can be generated. ACF profiles may be generated for different radiuses in the converted information. For example, for any one radius, the ACF profile may be plotted as a function of lag. Any peaks in the ACF profile may be identified as the periodic components. The peaks in the ACF profile may be identified in any suitable manner.

In another embodiment, identifying the periodic components includes determining an average magnitude difference function (AMDF) for different radiuses in the converted information and identifying the periodic components based on valleys in the AMDF. For example, identifying the periodic components may include calculating the AMDF for each radius image data vector and identifying the existence of the periodic components by AMDF valleys. In one such example, using the polar space information, a gray scale image of AMDF: Radius (mm) as a function of correlation lag (degree) can be generated. AMDF profiles may be generated for different radiuses in the converted information. For example, for any one radius, the AMDF profile may be plotted as a function of lag. Any valleys in the AMDF profile may be identified as the periodic components. The valleys in the AMDF profile may be identified in any suitable manner.

In some embodiments, identifying the periodic components includes performing a one-dimensional Fourier transform for different radiuses in the converted information to produce spectrums for the different radiuses and identifying peaks in the spectrums. For example, for transform domain filtering, identifying the periodic components may include performing a one-dimensional Fourier transform for each radius image data vector. The one-dimensional Fourier transform may be performed in any suitable manner. Each of the spectrums may include a plot of spectrum magnitude as a function of normalized frequency. Identifying the peaks in the spectrums may include checking the peaks in the spectrum and identifying the existence of periodic surface bump structures. Relatively strong periodic signal components may be detected by comparing the non-DC peak magnitudes with the average level. In spectrums of rows of an initial polar space defect map that do not contain periodic defects, no relatively strong periodic signal will be detected. In contrast, in spectrums of rows of an initial polar space defect map that do contain periodic defects, relatively strong periodic signals will be detected.

The method further includes determining if the periodic components correspond to defects on the substrate. For example, once the periodic components have been identified in the polar space information, the signals, image signals, data, image data, or other information corresponding to the periodic components may be plotted in a polar space target map that shows the signals, image signals, data, image data, or other information as a function of radius (mm) and angle (degree). The signals, image signals, data, image data, or other information in the target map may then be processed according to any suitable defect detection algorithm or method. For example, a threshold may be applied to the signals, image signals, data, image data, or other information, and any signals, image signals, data, image data, or other information above the threshold may be identified as a defect. Such defect detection may also be performed without generating a polar space target map.

In some embodiments, determining if the periodic components correspond to defects on the substrate includes estimating pitch and starting angle for the periodic components, defining search regions using the pitch and starting angle, and detecting defects in the search region. Such a determining step may be performed for instances in which the ACF or AMDF is used for the identifying step. For example, ACF and/or AMDF profiles may be plotted as a function of lag for different radiuses (e.g., one ACF and/or AMDF profile per radius), and the pitch can be estimated from the peaks of the ACF profiles or the valleys of the AMDF profiles or a combination of the ACF and AMDF signals. In this manner, the one-dimensional ACF and AMDF can be used to estimate the pitch of defects (such as bumps) in the substrate tangential (angular) direction. In addition, the pitch and the starting angle of the defects can be estimated from ACF or AMDF and then used to define the defect search regions on the substrate surface. In this manner, concentric bump defects may be detected in the specified substrate regions. Detecting the defects in the substrate regions may be performed as described further herein (e.g., using one or more defect detection algorithms and/or methods). As a result, more sensitive and pure periodic bump detection can be achieved. In addition, the defects (e.g., bump defects on concentric rings) may be reliably detected in the presence of a relatively noisy background in the polar space information (e.g., a polar space surface image).

In other embodiments, determining if the periodic components correspond to defects on the substrate includes suppressing non-peaks in the spectrums produced by the one-dimensional Fourier transform to produce filtered spectrums, inverse transforming the filtered spectrums to a spatial domain to obtain filtered image data, and detecting defects on the substrate using the filtered image data. In this manner, suppressing the non-peaks is performed in the transform domain, and the filtered image data may include periodic signal enhanced image data or the cleaned-up defect image data. For example, a filtered defect map of EPI crown defects in polar space may be generated. Such a filtered map in polar space may include filtered polar space defect positions (e.g., white spots against a black background) plotted as a function of radius in mm and angle in degrees. Such a filtered map may show multiple rings of EPI crowns after non-periodic defects have been removed by the Fourier transform domain processing. Detecting the defects using the filtered image data may be performed as described further herein (e.g., using one or more defect detection algorithms and/or methods). As a result, more sensitive and pure periodic bump detection can be achieved.

As described further herein, defect shape and defect orientation can be used to achieve improved detection sensitivity and purity for certain types of defects. In addition or alternatively, as described further herein, defect spatial distributions, including defect position distribution and defect shape/area distribution, are also important defect spatial characteristics that can be used in many cases to effectively improve the detection sensitivity and purity. In addition to defects such as EPI crown defects and SOI bump ring defects, the principles described herein are applicable for the detection of other wafer surface defects spatially located and formed according to certain regular rules.

Converting the information, identifying the periodic components, and determining if the periodic components correspond to defects on the substrate are performed using a computer system. The computer system may be further configured as described herein. In addition, a system configured to perform the methods described above may include such a computer system as well as an inspection system. The inspection system may be configured as described further herein and may be configured to generate the information for the substrate that is converted into polar space for use in the embodiments described herein. The inspection system may also include one of the WaferSight family of tools that are commercially available from KLA-Tencor and that has been modified such that the inspection system can perform the computer-implemented method(s) described herein. Furthermore, a non-transitory computer-readable medium such as those described further herein may store program instructions that are executable for performing the above-described computer-implemented methods.

Further modifications and alternative embodiments of various aspects of the invention will be apparent to those skilled in the art in view of this description. For example, methods and systems for detection of selected defects in relatively noisy inspection data are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for detecting defects on a substrate, comprising:
    applying a spatial filter algorithm to inspection data acquired across an area on the substrate to determine a first portion of the inspection data that has a higher probability of being a selected type of defect than a second portion of the inspection data, wherein the selected type of defect comprises a non-point defect, wherein the inspection data comprises inspection data generated by combining two or more raw inspection data corresponding to the same locations on the substrate, and wherein the raw inspection data that is combined is data acquired by inspection of the substrate that has not been processed to alter a signal-to-noise ratio of the data;
    generating a two-dimensional map illustrating the first portion of the inspection data;
    searching the two-dimensional map for an event that has spatial characteristics that match spatial characteristics of the selected type of defect; and
    determining if the event corresponds to a defect having the selected type, wherein said applying, said generating, said searching, and said determining are performed using a computer system.

2. The method of claim 1, wherein the two or more raw inspection data are generated by different detectors of the same inspection system.

3. The method of claim 1, wherein the two or more raw inspection data are generated by different detectors of the same inspection system, and wherein the different detectors are coupled to different collectors of the same inspection system.

4. The method of claim 1, wherein the two or more raw inspection data are generated by different detectors of the same inspection system, wherein the different detectors are configured to detect light scattered from the substrate at different scattering angles, and wherein the different detectors are not different detection elements of the same detector.

5. The method of claim 1, wherein the two or more raw inspection data are generated simultaneously.

6. The method of claim 1, wherein the two or more raw inspection data are generated sequentially.

7. The method of claim 1, wherein combining two or more raw inspection data comprises applying a mathematic function to the two or more raw inspection data corresponding to the same locations on the substrate.

8. The method of claim 1, wherein the spatial characteristics of the selected type of defect are determined based on processing of the substrate.

9. The method of claim 1, wherein said searching comprises applying a Hough transform to the two-dimensional map, and wherein the spatial characteristics of the selected type of defect are linear.

10. The method of claim 1, wherein said searching comprises applying a line enhancement filter to the two-dimensional map.

11. The method of claim 1, wherein the selected type of defect comprises slip lines.

12. The method of claim 1, wherein the selected type of defect comprises boat marks.

13. The method of claim 1, wherein the selected type of defect comprises straight line structures.

14. The method of claim 1, wherein the selected type of defect comprises defects having limited orientations and location regions defined by a material structure on the substrate and one or more processes performed on the substrate.

15. The method of claim 1, wherein the selected type of defect comprises defects having only specific orientations.

16. The method of claim 1, wherein the substrate comprises a wafer.

17. The method of claim 1, further comprising converting information generated by inspection of the substrate into polar space, identifying periodic components in the converted information, wherein the periodic components are not periodic components due to dies formed on the substrate or structures formed in the dies, and determining if the periodic components correspond to defects on the substrate.

18. A non-transitory computer-readable medium, storing program instructions executable on a computer system for performing a computer-implemented method for detecting defects on a substrate, wherein the computer-implemented method comprises:
    applying a spatial filter algorithm to inspection data acquired across an area on the substrate to determine a first portion of the inspection data that has a higher probability of being a selected type of defect than a second portion of the inspection data, wherein the selected type of defect comprises a non-point defect, wherein the inspection data comprises inspection data generated by combining two or more raw inspection data corresponding to the same locations on the substrate, and wherein the raw inspection data that is combined is data acquired by inspection of the substrate that has not been processed to alter a signal-to-noise ratio of the data;
    generating a two-dimensional map illustrating the first portion of the inspection data;
    searching the two-dimensional map for an event that has spatial characteristics that match spatial characteristics of the selected type of defect; and
    determining if the event corresponds to a defect having the selected type.

19. A system configured to detect defects on a substrate, comprising:
    an inspection subsystem comprising two or more detectors, wherein the two or more detectors are configured to detect light from the substrate and to generate raw inspection data in response to the detected light; and a computer subsystem configured for:

applying a spatial filter algorithm to inspection data acquired across an area on the substrate to determine a first portion of the inspection data that has a higher probability of being a selected type of defect than a second portion of the inspection data, wherein the selected type of defect comprises a non-point defect, wherein the inspection data comprises inspection data generated by combining two or more of the raw inspection data generated by the two or more detectors corresponding to the same locations on the substrate, and wherein the raw inspection data that is combined is data acquired by inspection of the substrate that has not been processed to alter a signal-to-noise ratio of the data;

generating a two-dimensional map illustrating the first portion of the inspection data;

searching the two-dimensional map for an event that has spatial characteristics that match spatial characteristics of the selected type of defect; and determining if the event corresponds to a defect having the selected type.

20. The system of claim 19, wherein the two or more raw inspection data are generated by different detectors of the two or more detectors of the inspection subsystem.

21. The system of claim 19, wherein the two or more raw inspection data are generated by different detectors of the two or more detectors of the inspection subsystem, and wherein the different detectors are coupled to different collectors of the inspection subsystem.

22. The system of claim 19, wherein the two or more raw inspection data are generated by different detectors of the two or more detectors of the inspection subsystem, wherein the different detectors are configured to detect light scattered from the substrate at different scattering angles, and wherein the different detectors are not different detection elements of the same detector.

23. The system of claim 19, wherein the two or more raw inspection data are generated simultaneously.

24. The system of claim 19, wherein the two or more raw inspection data are generated sequentially.

25. The system of claim 19, wherein combining the two or more raw inspection data comprises applying a mathematic function to the two or more raw inspection data corresponding to the same locations on the substrate.

26. The system of claim 19, wherein the spatial characteristics of the selected type of defect are determined based on processing of the substrate.

27. The system of claim 19, wherein said searching comprises applying a Hough transform to the two-dimensional map, and wherein the spatial characteristics of the selected type of defect are linear.

28. The system of claim 19, wherein said searching comprises applying a line enhancement filter to the two-dimensional map.

29. The system of claim 19, wherein the selected type of defect comprises slip lines.

30. The system of claim 19, wherein the selected type of defect comprises boat marks.

31. The system of claim 19, wherein the selected type of defect comprises straight line structures.

32. The system of claim 19, wherein the selected type of defect comprises defects having limited orientations and location regions defined by a material structure on the substrate and one or more processes performed on the substrate.

33. The system of claim 19, wherein the selected type of defect comprises defects having only specific orientations.

34. The system of claim 19, wherein the substrate comprises a wafer.

35. The system of claim 19, wherein the computer subsystem is further configured for converting information generated by inspection of the substrate into polar space, identifying periodic components in the converted information, wherein the periodic components are not periodic components due to dies formed on the substrate or structures formed in the dies, and determining if the periodic components correspond to defects on the substrate.

* * * * *